United States Patent
Eidenschink et al.

(10) Patent No.: US 12,167,843 B2
(45) Date of Patent: Dec. 17, 2024

(54) PATENT FORAMEN OVALE (PFO) TUNNEL FILLER

(71) Applicant: St. Jude Medical, Cardiology Division, Inc., St. Paul, MN (US)

(72) Inventors: Tracee Eidenschink, Wayzata, MN (US); Theodore P. Dale, Corcoran, MN (US); Linda Cornelius, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 167 days.

(21) Appl. No.: 17/368,507

(22) Filed: Jul. 6, 2021

(65) Prior Publication Data
US 2022/0008051 A1 Jan. 13, 2022

Related U.S. Application Data

(60) Provisional application No. 63/048,700, filed on Jul. 7, 2020.

(51) Int. Cl.
*A61B 17/00* (2006.01)

(52) U.S. Cl.
CPC ........ *A61B 17/0057* (2013.01); *A61B 2017/00579* (2013.01); *A61B 2017/00592* (2013.01); *A61B 2017/0065* (2013.01)

(58) Field of Classification Search
CPC ...... A61B 17/0057; A61B 2017/00579; A61B 2017/00592; A61B 2017/0065; A61B 2017/00597; A61B 2017/00654; A61B 2017/00601; A61B 2017/00575; A61F 2/0063; A61F 2002/0068
See application file for complete search history.

(56) References Cited

U.S. PATENT DOCUMENTS

| | | | | |
|---|---|---|---|---|
| 5,634,936 | A * | 6/1997 | Linden | A61L 31/14 604/60 |
| 2002/0077661 | A1 * | 6/2002 | Saadat | A61F 2/08 606/221 |
| 2004/0220596 | A1 * | 11/2004 | Frazier | A61B 17/0057 606/153 |
| 2007/0270905 | A1 | 11/2007 | Osborne | |
| 2008/0058866 | A1 | 3/2008 | Young et al. | |
| 2009/0118745 | A1 * | 5/2009 | Paul, Jr. | A61B 17/0057 606/151 |
| 2010/0057191 | A1 * | 3/2010 | Pavcnik | A61F 2/2475 623/1.36 |

(Continued)

FOREIGN PATENT DOCUMENTS

WO 2008021969 A2 2/2008

OTHER PUBLICATIONS

Extended European Search Report EP Application No. 21184173.9, mailed Nov. 25, 2021, 11 pages.

*Primary Examiner* — Diane D Yabut
(74) *Attorney, Agent, or Firm* — Armstrong Teasdale LLP

(57) ABSTRACT

A patent foramen ovale (PFO) tunnel filler medical device including device anchors coupled to and extending outwardly from a filler portion of a device frame that has a generally planar shape configured to fill a PFO tunnel, and a delivery system including the same are described herein. The medical device includes a fabric layer and the device anchors are configured to extend outwardly from the device frame.

13 Claims, 5 Drawing Sheets

(56) References Cited

U.S. PATENT DOCUMENTS

2014/0330295 A1* 11/2014 Lecuivre ................. A61L 27/34
606/151
2015/0005809 A1    1/2015 Ayres et al.
2016/0331382 A1* 11/2016 Center ............. A61B 17/12177

* cited by examiner

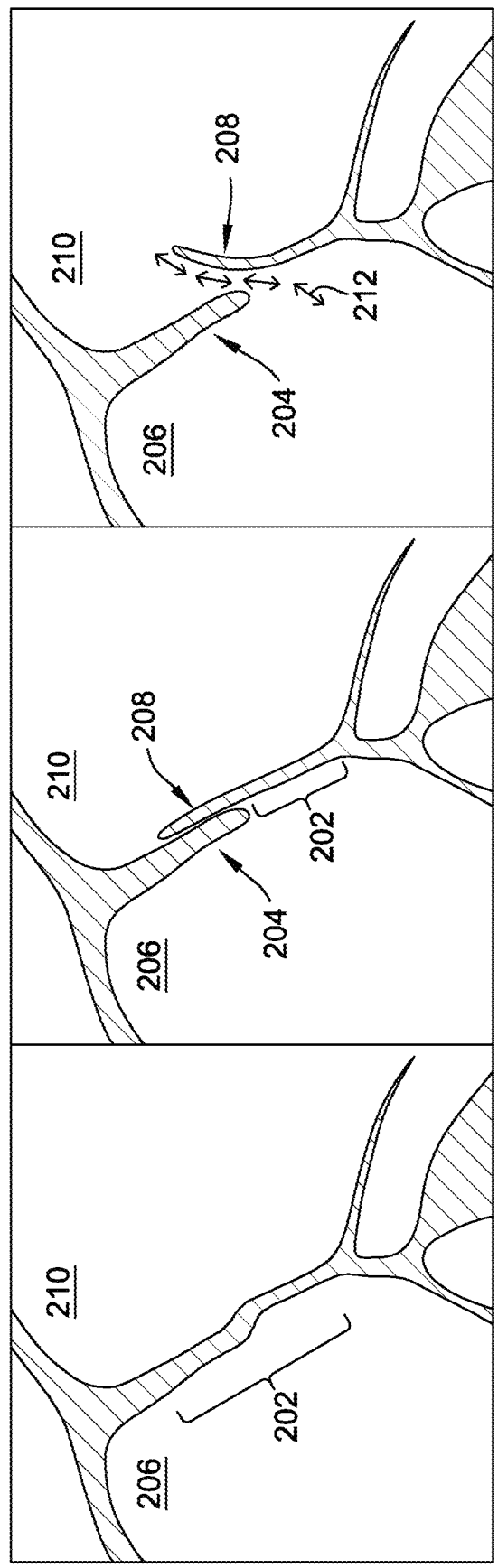

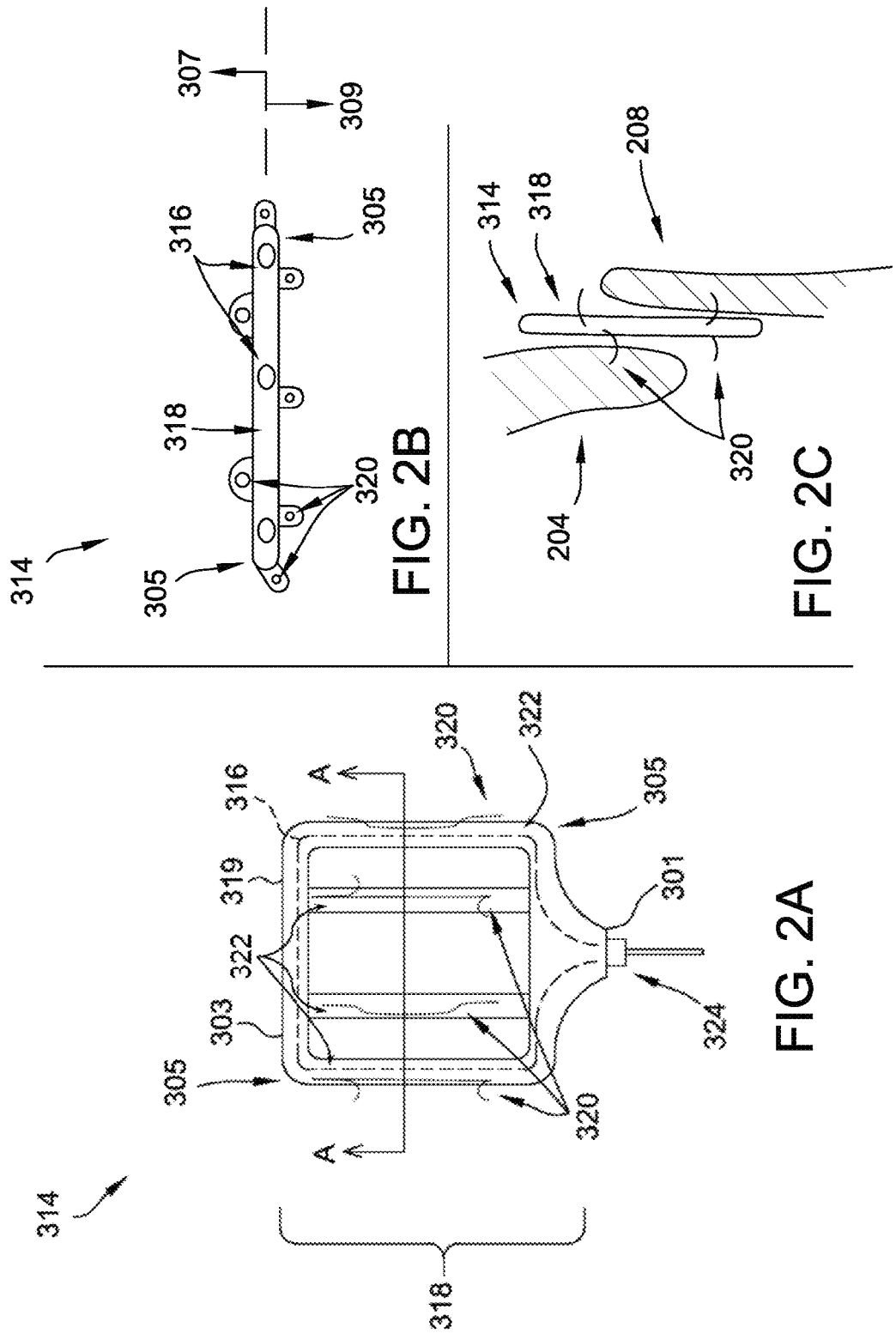

PATENT FORAMEN OVALE (PFO) TUNNEL FILLER

CROSS-REFERENCE TO RELATED APPLICATIONS

The present application claims the benefit of priority to U.S. Provisional Patent Application No. 63/048,700, filed Jul. 7, 2020, the entire contents of which is hereby incorporated by reference in its entirety.

BACKGROUND OF THE DISCLOSURE

A. Field of Disclosure

The present disclosure relates generally to medical devices that are used in the human body. In particular, the present disclosure is directed to anchored and internally filled portions medical devices that are delivered to a target site, such as a patent foramen ovale (PFO), within the human body. More specifically, the present disclosure is directed to anchoring an internally filled medical device within the PFO in order to seal the PFO tunnel track and prevent transfer between chambers of the heart.

B. Background

A wide variety of medical devices are used to treat any target site, such as an abnormality, a vessel, an organ, an opening, a chamber, a channel, a hole, a cavity, or the like, located anywhere in the body. For instance, a patent foramen ovale (PFO) target site is a flap-type opening that is prevalent in 10-20% of the population and may be closed at any age. With more and more procedures becoming percutaneous, several percutaneous procedures must cross the septal wall to access the left atrium. While not all PFO's require closure, younger people getting a PFO closed may develop conditions when they are older (e.g., AFIB) whose treatment requires crossing the septal wall to either map, ablate, or place an LAA closure device, for example. Conventional PFO closure solutions include a web of nitinol (e.g., in an umbrella/double-disc design) that must be navigated in order to cross the septal wall.

Accordingly, it would be desirable to close a PFO by filling and sealing the tunnel track itself (as an alternative to or in conjunction with closure devices that are configured to block both sides of the PFO using the umbrella/double-disc design) by anchoring an internally filled medical device into the PFO tunnel. Additionally, it would be desirable to close a PFO with a medical device that allows for easier subsequent crossing through the septal wall to access the left atrium, and that leaves less metal behind.

BRIEF SUMMARY OF THE DISCLOSURE

In one embodiment, the present disclosure is directed to a medical device for treating a patent foramen ovale (PFO) target site. The medical device includes a device frame having a generally planar shape configured to fill a PFO tunnel and formed from a shape memory material, wherein the device frame comprises a filler portion. The device further includes at least one fabric layer covering the filler portion of the device frame.

In another embodiment, the present disclosure is directed to a delivery system including a medical device and a delivery sheath. The medical device includes a device frame having a generally planar shape corresponding to a shape of a patent foramen ovale (PFO) tunnel and formed from a shape memory material, wherein the device frame comprises a filler portion; at least one fabric layer; and a plurality of device anchors extending outwardly from the device frame and coupled to at least one of the device frame and the at least one fabric layer. The delivery system further includes a delivery sheath configured to retain and recapture the medical device during deployment of the medical device to a PFO target site.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 1A is an illustration of a general shape of a normal fossa ovalis side view in accordance with the present disclosure. FIG. 1B is an illustration of a general shape of a closed PFO side view in accordance with the present disclosure. FIG. 1C is an illustration of a general shape of an open PFO side view in accordance with the present disclosure.

FIG. 2A is an exemplary embodiment of a planar surface view of a PFO tunnel filler medical device in accordance with the present disclosure. FIG. 2B depicts a top view of the device shown in FIG. 2A. FIG. 2C depicts a side view of the device shown in FIG. 2A, when deployed.

Corresponding reference characters indicate corresponding parts throughout the several views of the drawings. It is understood that that Figures are not necessarily to scale.

DETAILED DESCRIPTION OF THE DISCLOSURE

Figure 2D:
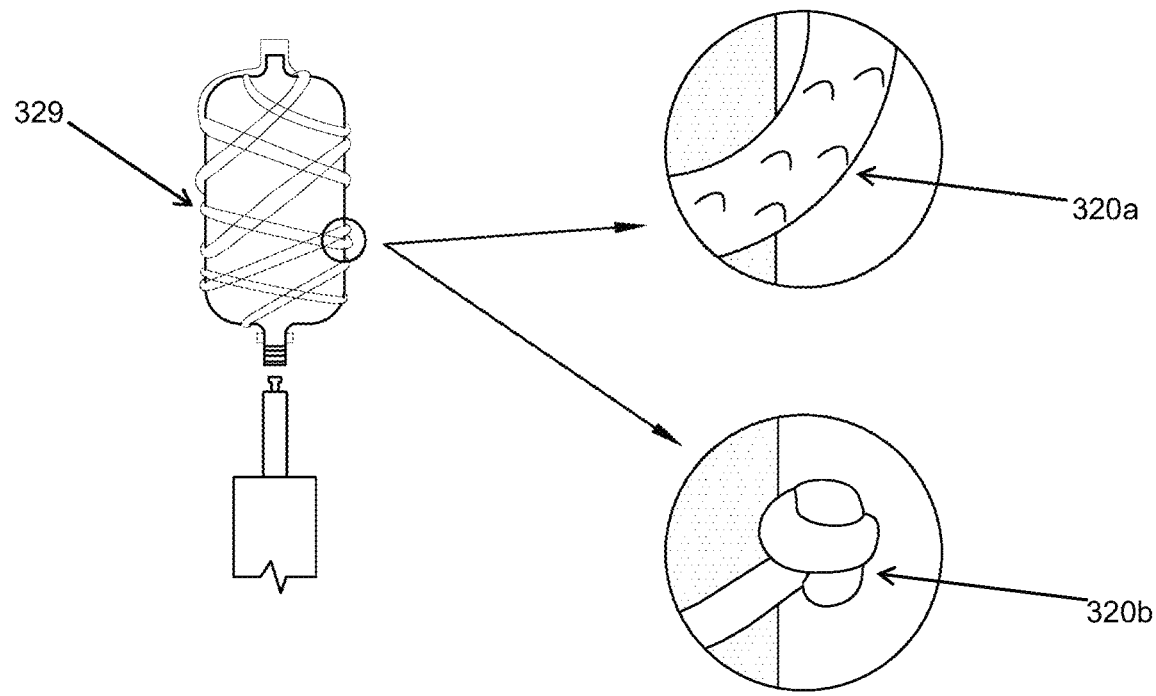
FIG. 2D is an exemplary embodiment of formed device anchors in accordance with the present disclosure.

The present disclosure generally relates to anchored and internally filled medical devices for treating a target site. Described herein are medical devices having device anchors extending outwardly from an internally filled portion of a frame of the device to engage patent foramen ovale (PFO) tunnel tissue at a PFO target site. Accordingly, the medical devices of the present disclosure enable suitable filling and sealing of the PFO tunnel track itself, with device anchors providing tunnel tissue engagement and dislodgement prevention of the medical devices while allowing easier crossing through the septal wall to the left atrium.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as a patent foramen ovale, a left atrial appendage, an atrial septal defect, a lesion, a vessel dissection, or a tumor. Embodiments of the medical device may be useful, for example, for occluding a PFO, LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

FIG. 1A shows a side view of a continuous track of tissue, fossa ovalis 202, forming a normal atrial wall that seals right atrium 206 and left atrium 210 from one another and prevents flow between the atrial chambers (206 and 210). In a normal heart, the septum secundum of the right atrium and the septum primum of the left atrium are fused together at birth, thus forming fossa ovalis 202. In contrast, FIGS. 1B and 1C respectively show open and shut PFO (i.e., unformed fossa ovalis) configurations. FIG. 1B shows an atrial wall side view in which septum secundum 204 of right atrium 206 and septum primum 208 of left atrium 210 overlap with one another but are not fused together, thus forming a closed/shut configuration of a PFO. During contraction/beating of the heart, the unformed fossa ovalis flaps open and shut, creating the PFO that allows unwanted blood flow between the left and right atrial chambers (206 and 210). FIG. 1C shows an atrial wall side view with a PFO 212 in an open configuration, thus illustrating the unwanted blood flow occurring between the atrial chambers 206, 210 via the PFO 212.

Turning now to FIG. 2A-C, an exemplary embodiment of a tunnel filler medical device 314 is shown in accordance with the present disclosure. Device 314 comprises a device frame 316 formed from a shape memory material. In an exemplary embodiment, device frame 316 is formed from a shape memory alloy. One particular shape memory alloy that may be used is Nitinol. In another exemplary embodiment, device frame 316 is formed from a polymer. In some embodiments, the polymer is a shape memory polymer and/or a bio-absorbable polymer. Device frame 316 comprises a body or filler portion 318 that is configured to sit within the PFO tunnel when deployed, thereby filling and effectively occluding the PFO tunnel. In some embodiments, filler portion 318 includes device frame 316 internally filled with a filler material (e.g., an occlusive fabric, not shown).

Device 314 further comprises a fabric layer 319 configured to cover/encase filler portion 318. Fabric layer 319 can include metal fabric, polymer fabric, metal mesh, polymer mesh, braided wire, woven wire, braided polymer, woven polymer, nonwoven polymer, other occlusive fabric, and combinations thereof. Depending on the embodiment, fabric layer 319 may be formed from a shape memory alloy (e.g., Nitinol), a shape memory polymer, a bio-absorbable polymer, and/or at least one of a polyurethane, pebax, nylon, PET, or PE material. In some embodiments, fabric layer 319 comprises at least one fabric layer. For example, fabric layer 319 may comprise an internal layer and an external layer, such that an internal layer is formed over and covers device frame 316, and an external layer is formed over and covers the internal layer (not shown). In an embodiment, the internal layer may be formed from metal while the external layer may be formed from polymer. In another embodiment, the internal layer may be formed from polymer while the external layer may be formed from metal. In yet another embodiment, both the internal and external layers may be formed from metal. In a further embodiment, both the internal and external layers may be formed from polymer.

In exemplary embodiments, neither device 314 nor filler portion 318 is configured to extend into the left atrial chamber to any significant extent when device 314 is deployed. In other words, a majority of filler portion 318 of device 314, when deployed, remains in and fills/occludes the PFO tunnel track. In other embodiments, filler portion 318 may extend a few millimeters into the left atrial chamber without adversely affecting the performance of the device (e.g., as depicted in FIG. 2C).

In exemplary embodiments, device 314 has a generally planar shape owing to a generally planar configuration of device frame 316, which serves to effectively fill and occlude the PFO tunnel when deployed. FIG. 2B depicts a sectional view of device 314 taken at line A-A of FIG. 2A. Depending on the embodiment, the generally planar shape may be a generally flat planar shape, a generally curved planar shape, or a combination thereof.

In some embodiments, device 314 further comprises a plurality of device anchors 320 coupled to and extending outwardly from device frame 316 and through fabric layer 319. In other embodiments, device anchors 320 may be coupled to and extend outwardly from fabric layer 319. Depending on the embodiment, such as when fabric layer 319 comprises an internal layer and an external layer, device anchors 320 may be: coupled to the external layer only, coupled to the internal layer only and extending through the external layer, or coupled to the internal layer extending through the external layer as well as coupled to the external layer. In yet other embodiments, device anchors 320 may be coupled to both device frame 316 as well as fabric layer 319. In an exemplary embodiment, there may be two, three, four, or more device anchors 320 coupled to device frame 316 and/or the at least one fabric layer 319, thus providing increased levels of anchoring for device 314 as desired. In an exemplary embodiment, device anchors 320 are formed from a shape memory alloy or stainless steel. Some particular shape memory alloys that may be used include Nitinol and MP35. In another exemplary embodiment, device anchors 320 are formed from a polymer. In some embodiments, the polymer is a shape memory polymer and/or a bio-absorbable polymer.

As shown in the exemplary embodiment of FIG. 2A-C, device anchors 320 are located on multiple sides of device 314. Specifically, device anchors 320 are coupled to multiple sides of device frame 316 (FIG. 2A-C). For example, on the generally planar shape of device 314, device anchors 320 are coupled to device frame 316 near both a proximal end 301 (i.e., a bottom end) and a distal end 303 (i.e., a top end) of device 314, along the side edges 305 of device 314, and on both planar faces (a front planar surface 307 and a back planar surface 309) of device 314 (as shown in FIG. 2A-B). In some embodiments, when device 314 is deployed, front planar surface 307 is configured to face the septum primum 208 of the left atrium 210, while back planar surface 309 is configured to face the septum secundum 204 of right atrium 206. In alternative embodiments, when device 314 is deployed, front planar surface 307 is configured to face the septum secundum 204 of right atrium 206, while back planar surface 309 is configured to face the septum primum 208 of the left atrium 210.

Depending on the embodiment, device anchors 320 may be sewn onto device frame 316, injection molded onto device frame 316, or coupled to device frame 316 using a combination of sewing and injection molding (not shown). In some embodiments, device anchors 320 may, additionally or alternatively, be incorporated into and/or onto fabric layer 319. FIG. 2D shows one or more metal (e.g., wire) or polymer strands 329 that are used to form fabric layer 319 for underlying device frame 316 (not shown). It is understood that a braided or woven fabric layer 319 on device 314 would include additional braided or woven metal or polymer strands 329 than are shown in FIG. 2D. In some embodiments, device anchors 320 may be formed as part of device 314 by one or more braided knurls/knots/loops (e.g., knurled device anchor 320a and knotted anchor device 320b, FIG. 2D). For example, metal or polymer strands 329 may form fabric layer 319 by attaching one strand with another strand such that a resultant braided or woven fabric layer 319 includes both a lighter/softer strand braid and a heavier/stiffer strand braid within a single braided layer or in two (or more) distinct layers of braid. In some embodiments, knurled wire 320a may be incorporated into metal or polymer strands 329 after it has been formed as fabric layer 319 over device frame 316. Depending on the embodiment, a device anchor formed from a knurled strand may include at least one of grooved, scaled, criss-crossed, and hatched strand. In some embodiments, knotted device anchors 320b may also be applied in a flat pattern across filler portion 318 of device 314.

In some embodiments, device anchors 320 may be formed as part of fabric layer 319 by co-braiding metal and/or polymer strands together, and subsequently cutting the co-braided metal/polymer strand to form device anchors 320 (e.g., hooks formed from cut wire, shown herein below in FIGS. 4B-C). Knurls, knots (such as 320a and 320b shown in FIG. 2D) and/or loops (such as 320 shown in FIG. 2B) purposely formed in/on at least one of the metal or polymer strands 329 may themselves serve as device anchors 320. In some embodiments, knurls/knots/loops may be cut off to expose free ends to serve as device anchors 320 (e.g., hooks and/or barbs, discussed below).

Figure 2E:
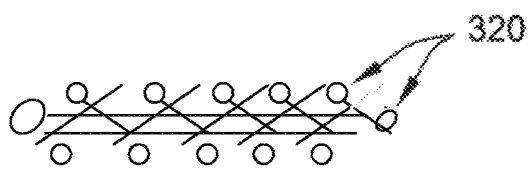
FIG. 2E and FIG. 2G depict top views of a device having two or more arrays of aligned or "in-sync" device anchors.
Figure 2F:
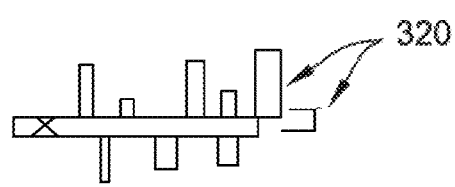
FIG. 2F and FIG. 2H depict top views of a device having two or more arrays of misaligned or "out-of-sync" device anchors.
Figure 2G:
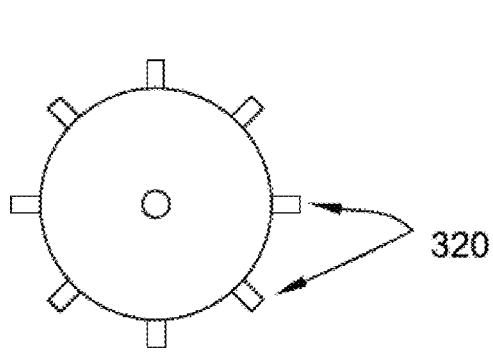
Figure 2H:
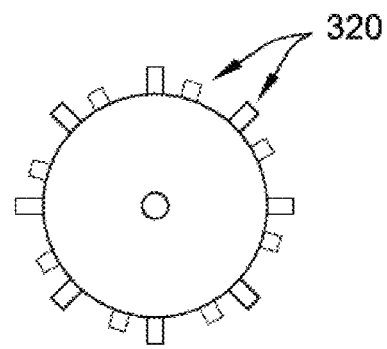

FIGS. 2E-2G show top (i.e., distal end) views of device 314, such as the device shown in FIG. 2D. FIGS. 2E and 2G depict devices having two or more arrays of aligned or in-sync device anchors 320, while FIGS. 2F and 2H depict devices having two or more arrays of misaligned or out-of-sync device anchors 320 (e.g., to allow for more contact points with tissue within the PFO tunnel). It is noted that while FIGS. 2E-2F depict a top view of a generally planar shape of device 314, this is for illustrative purposes of knurl/knot/loop device anchors 320. Exemplary embodiments of device 314 will have a top view in accordance with a generally planar configuration of formed device frame 316, such that device 314 including filler portion 318 is properly shaped to fill the PFO tunnel and occlude flow between the left and right atrial chambers of the heart. In some embodiments, device 314 may comprise an inflatable device (e.g., like a balloon) in order to block/fill the PFO tunnel once deployed. In these embodiments, device 314 may have a circular-shaped top view (see FIGS. 2G and 2H), a near-circular top view (e.g., elliptical-shaped), or other shaped top view based on various shapes and configurations of balloons known in the art. Upon deployment, it is noted that a top (distal view) of device 314 may be based on the shape of the PFO tunnel being filled by the device and the conformance of the device to the surrounding tissue.

In some embodiments, device anchors 320 comprise hooks that may have uniform or varying sizes, and/or uniform or varying hook geometries. Hook size may vary depending on length and/or width of each hook. Hook geometry may vary based on straight and/or curved hook segments, as well as hook orientation/direction. In some embodiments, hook orientation/direction is uniform. That is, every hooked device anchor 320 coupled to the tunnel filler medical device 314 is pointed/oriented in the same direction in order to prevent migration of device 314 out of the PFO tunnel into the left and right atrial chambers. In some embodiments, every hook on a particular end, side, and/or planar surface of the device may have a uniform orientation, while hooks on another (e.g., opposing) end or side may have another (e.g., opposing) orientation. For example, hooks on a front planar surface of the device may have a uniform downward-hooked orientation, while hooks on a back planar surface of the device may have a uniform upward-hooked orientation, or vice versa. In some embodiments, hooks on a particular end, side, and/or planar surface of the device may have multiple different orientations/directions. For example, hooks on one (or more) planar surface(s) of the device may include both hooks with an upward-hooked orientation as well as hooks with a downward-hooked orientation.

In some embodiments, device anchors 320 comprise barbs, or sharp projections extending out from device 314. Depending on the embodiment, barbs may have uniform or varying sizes, and/or uniform or varying orientations. Barb size may vary depending on height and/or width of each barb. Barb orientation may vary based on the direction in which the barb is pointed. In some embodiments, device anchors 320 comprise at least one hook and at least one barb. In some embodiments, device anchors 320 may be retractable and/or displaceable with an expanded or contracted configuration of device 314.

In some embodiments, filler portion 318 of device 314 further comprises at least one channel 322 (see FIG. 2A) formed within device frame 316 or fabric layer 319, and wherein device anchors 320 extend out of the at least one channel 322. In some embodiments, device anchors 320 are formed in pairs (e.g., a length of wire hooked at both ends) such that each device anchor 320 is connected to another device anchor 320, a connector between the two is seated within channel 322, and each device anchor 320 extends out of channel 322 to extend outwardly from device frame 316. For example, in some embodiments, channels 322 are formed in fabric layer 319 as pockets for insertion of device anchors 320.

Device 314 also includes a delivery member 324 located on a proximal end of filler portion 318 (which is also proximal end 301 of device 314 in the embodiment of FIG. 2A) and configured to be connected to a delivery cable for delivery and deployment at the PFO target site. Following deployment, the delivery cable is disconnected from delivery member 324, and may be subsequently reconnected for retrieval of device 314 if necessary.

In exemplary embodiments, tunnel filler medical device 314 is placed within the PFO tunnel upon deployment to provide proper filling and sealing of the PFO tunnel (and therefore PFO closure). For example, FIG. 2C shows a deployed side view of device 314 in which filler portion 318 is seated within the PFO tunnel and anchored to both the septum secundum 204 and septum primum 208 via device anchors 320.

Figure 3B:
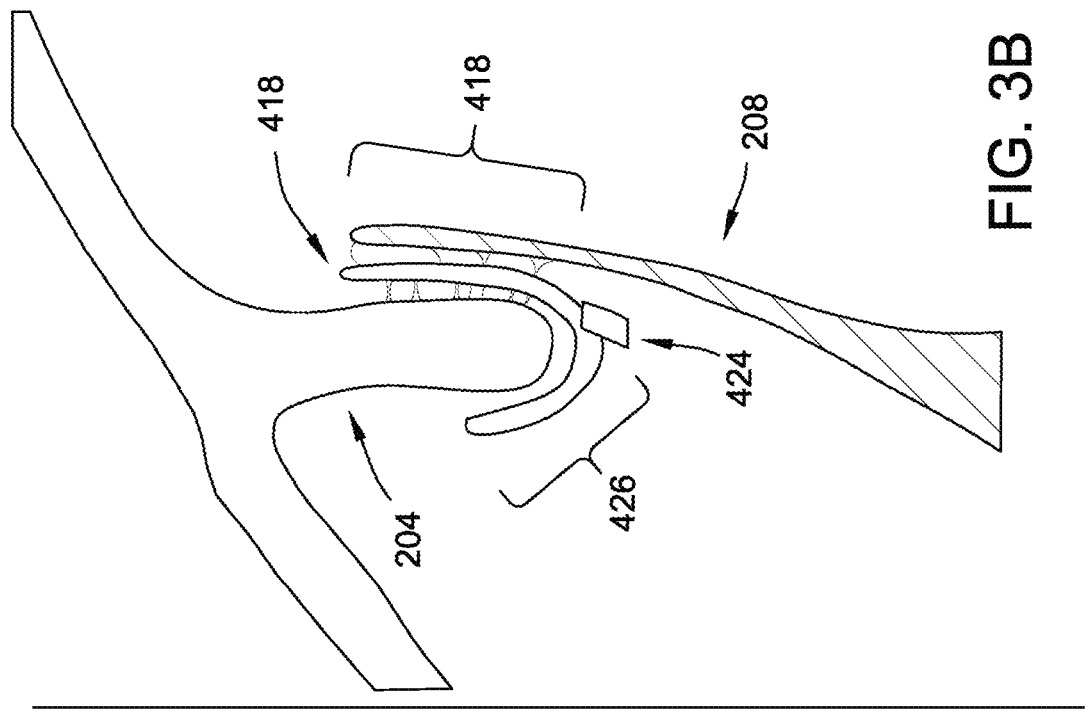
FIG. 3B depicts a side view of the device shown in FIG. 3A, when deployed.
Figure 3A:
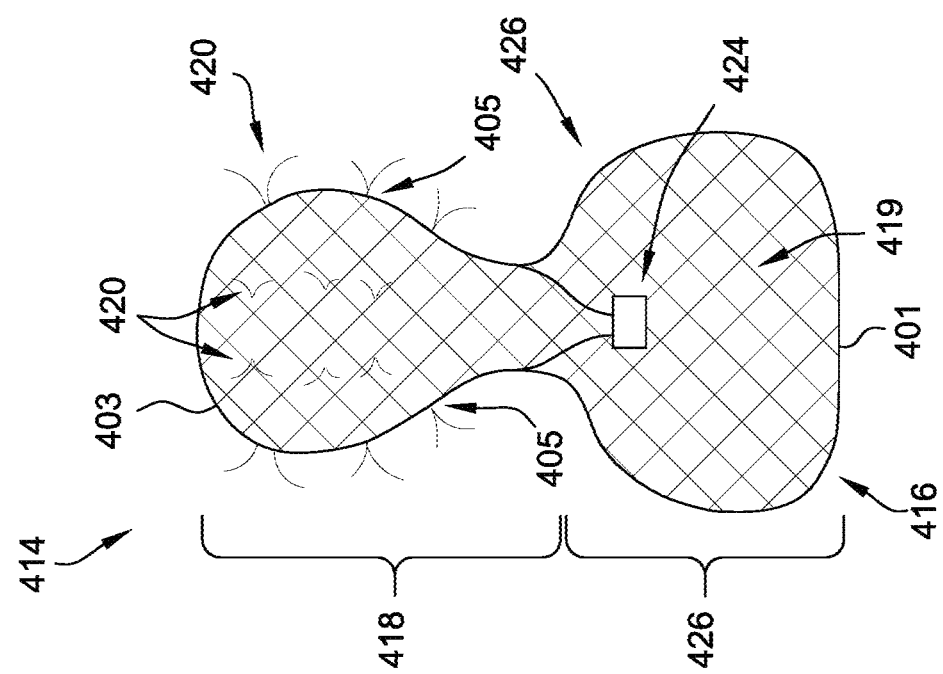
FIG. 3A is another exemplary embodiment of a planar surface view of a PFO tunnel filler medical device including a tissue fixation portion in accordance with the present disclosure.

FIG. 3A shows another exemplary embodiment of a planar surface of a tunnel filler medical device 414 shown with fabric layer 419. Similar to fabric layer 319 above, fabric layer 419 can include metal fabric, polymer fabric, metal mesh, polymer mesh, braided wire, woven wire, braided polymer, woven polymer, nonwoven polymer, other occlusive fabric, and combinations thereof. Depending on the embodiment, fabric layer 419 may be formed from a shape memory alloy (e.g., Nitinol), a shape memory polymer, a bio-absorbable polymer, and/or at least one of a polyurethane, pebax, nylon, PET, or PE material. In some embodiments, fabric layer 419 comprises at least one fabric layer, such as an internal layer formed over device frame 416, and an external layer formed over the internal layer (not shown). Depending on the embodiment, the internal layer may be formed from metal while the external layer may be formed from polymer, the internal layer may be formed from polymer while the external layer may be formed from metal, both the internal and external layers may be formed from metal, or both the internal and external layers may be formed from polymer.

While similar to device 314 shown in FIG. 2A-C, device 414 includes an additional tissue fixation portion 426 proximal to filler portion 418. Tissue fixation portion 426 is configured to wrap around, affix to, and/or cover over the right atrial tunnel side of the PFO, to further ensure placement and anchoring of device 414 and, therefore, ensure sealing and closure of the PFO. Depending on the embodiment, tissue fixation portion 426 may comprise one or more flap portions. In exemplary embodiments, tissue fixation portion 426 may further include fabric layer 419, as extended from filler portion 418, such that the entire device frame 416 is covered with fabric layer 419. In some embodiments, internal and external layers (not shown) of fabric layer 419 may be present such that internal and/or external layers also extend from filler portion 418 to cover tissue fixation portion 426. That is, in embodiments when fabric layer 419 comprises an internal layer and external layer, the internal layer may extend from filler portion 418 to cover tissue fixation portion 426 while the external layer does not extend past filler portion 418, or the external layer may extend from filler portion 418 to cover tissue fixation portion 426 while the internal layer does not extend past filler portion 418, or both the internal and external layers of fabric layer 319 may extend from filler portion 418 to cover tissue fixation portion 426. In some embodiments, fabric layer 419 may only cover filler portion 418 while tissue fixation portion 426 remains uncovered (e.g., is formed only from an extension of device frame 416). In exemplary embodiments, device anchors 420 are only coupled at filler portion 418 of device frame 416, while tissue fixation portion 426 is free of device anchors 420. In some embodiments, tissue fixation portion 426 may further include at least one device anchor 420 coupled to and extending outwardly from tissue fixation portion 426 of device 414, to maintain tissue fixation portion placement once deployed. In embodiments where fabric layer 419 extends from filler portion 418 to cover tissue fixation portion 426, device anchors 420 extending from tissue fixation portion 426 may be coupled to device frame 416 and/or fabric layer 419.

Also, similar to device anchors 320, device 414 comprises device anchors 420 that may be located on proximal 401 and distal end 403, side edges 405, and/or front and back planar faces (not shown) of device 414 in order to engage tissue in the PFO tunnel. In some embodiments, device 414 further includes fabric layer 419 configured to cover device frame 416 such that device anchors 420 coupled to filler portion 418 (e.g., device anchors 420 attached to device frame 416 and/or fabric layer 419 of filler portion 418) and device anchor(s) 420 coupled to tissue fixation portion 426 (e.g., device anchors 420 attached to device frame 416 and/or fabric layer 419 of tissue fixation portion 426) extend outwardly through/from fabric layer 419 for adequate tissue anchoring. Fabric layer 419 aids in proper placement of tissue fixation portion 426 around the septum secundum 204 and may comprise metal, polymer, and/or other occlusive material as described above. In exemplary embodiments, tissue fixation portion 426 prevents device 414 from migrating/dislocating out of the PFO tunnel toward the left atrium, while device anchors 420 prevent device 414 from migrating/dislocating out of the PFO tunnel toward the right atrium.

Delivery member 424 is similar to delivery member 324 shown in FIG. 2A. However, with the additional tissue fixation portion 426, delivery member 424 is more centrally located between proximal and distal ends 401, 403 of device 414. Delivery member 424 is located approximately mid-device and proximal to filler portion 418 and distal to tissue fixation portion 426 in order to enable accurate deployment of each portion, as shown in FIG. 3B and described herein below.

FIG. 3B shows a side view of device 414 shown in FIG. 3A when deployed in a PFO tunnel. Similarly to the deployed view of device 314 shown in FIG. 2C, device 414 (including filler portion 418) is seated within the PFO tunnel and anchored (via device anchors 420) to both the septum secundum 204 and septum primum 208. In the deployed configuration, tissue fixation portion 426 is wrapped around the septum secundum 204 in order to seal the right side (i.e., right atrial chamber side) of the PFO tunnel. Delivery member 424 is seen in FIG. 3B in its deployed position.

In other exemplary embodiments, a delivery system comprises a tunnel filler medical device as described herein above and a delivery sheath configured to retain and recapture the medical device during deployment of the medical device to a patent foramen ovale (PFO) target site. The tunnel filler medical device includes a device frame having a generally planar shape configured to fill a PFO tunnel and formed from a shape memory material, wherein the device frame comprises a filler portion having a fabric layer, and a plurality of device anchors coupled to and extending outwardly from the device frame.

Figure 4A:
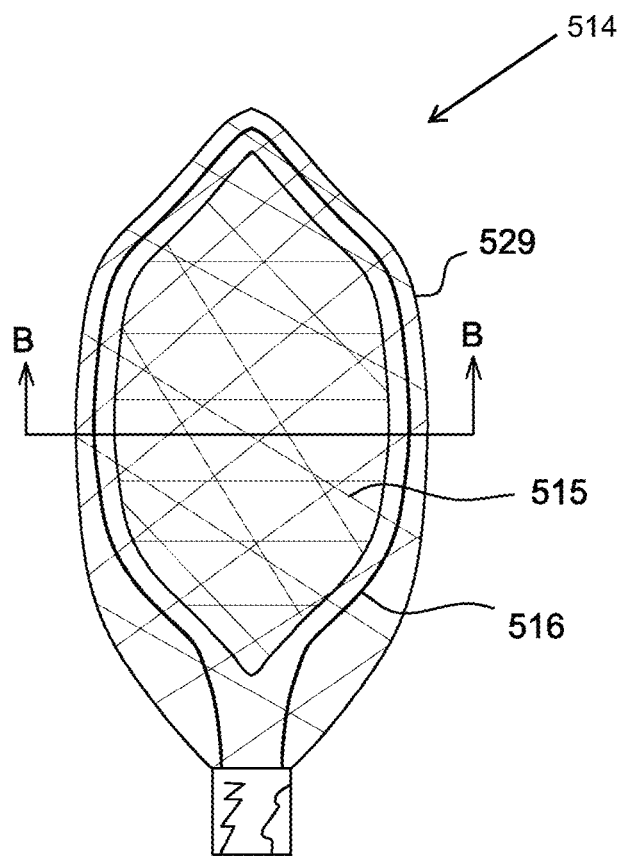
FIG. 4A is yet another exemplary embodiment of a planar surface view of a PFO tunnel filler medical device in accordance with the present disclosure.
Figure 4B:
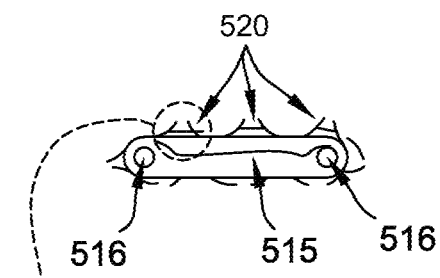
FIG. 4B depicts a top view of the device shown in FIG. 4A.
Figure 4C:
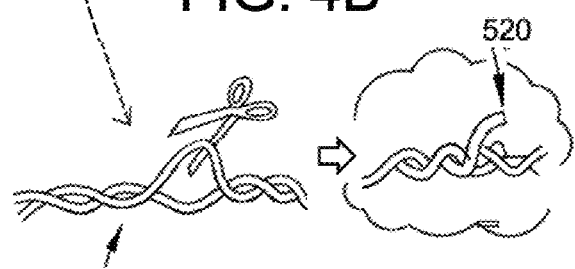
FIG. 4C depicts formation of device anchors shown in FIG. 4B.

Turning now to FIG. 4A-C, an exemplary embodiment of a tunnel filler medical device 514 is shown in accordance with the present disclosure. Device 514 comprises a device frame 516 internally filled with a filler material 515, and covered with metal or polymer strands 529 (similar to metal or polymer strands 329 shown in FIG. 2D). Metal or polymer strands 529 that form a fabric layer (such as fabric layer 319, 419) to cover the underlying device frame 516 are used to construct or create integrated device anchors 520 (such as anchoring hooks). It is understood that device 514 having metal or polymer strands 529 used to form a (e.g., braided or woven) fabric layer, as described herein above, would include additional metal or polymer strands 529 than are shown in FIG. 4A. In some embodiments, one or more purposely-formed loops of metal (e.g., wire) or polymer strands 529 may be cut to create a hook to serve as a device anchor 520, as shown in FIGS. 4C and 4B. FIG. 4C shows an embodiment in which larger loops are formed in metal or polymer strands 529, then cut. In this embodiment, a cut, free end of wire/polymer may now be employed as device anchor 520 (e.g., a hooked device anchor formed from the cut, free end of wire or polymer strand). Depending on the embodiment, a larger loop may be cut to form either one or two device anchors, for example by varying the location at which the larger loop is cut and/or by varying the number of cuts made. Further, depending on the desired length of device anchor(s) 520, at least a portion of the larger loop may be removed when cut.

While embodiments of the present invention have been described, it should be understood that various changes, adaptations and modifications may be made therein without departing from the spirit of the invention and the scope of the appended claims. For example, it is anticipated that the filler portion could be concave, convex, tapered, or a combination of shapes without departing from the invention herein. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a patent foramen ovale (PFO) target site, the medical device comprising:
    a device frame having a generally planar shape configured to fill and remain substantially within a PFO tunnel, the device frame being formed from a shape memory material, wherein the device frame comprises a filler portion having a front planar surface and a back planar surface, wherein a distal end of the filler portion defines a distalmost end of the device frame and is configured to remain within the PFO tunnel when the medical device is deployed;
    a plurality of device anchors extending outwardly from the filler portion on both the front planar surface and the back planar surface; and
    at least one fabric layer covering the filler portion of the device frame, the at least one fabric layer having a plurality of channels defined therein, wherein each channel of the plurality of channels extends from the distal end of the filler portion to a proximal end of the filler portion, and wherein each device anchor of the plurality of device anchors is coupled to the at least one fabric layer and extends outwardly through the at least one fabric layer from a corresponding channel of the plurality of channels.

2. The medical device of claim 1, wherein the shape memory material is selected from nitinol and MP35.

3. The medical device of claim 1, wherein the shape memory material comprises a polymer.

4. The medical device of claim 1, wherein the at least one fabric layer comprises at least one of metal fabric, polymer fabric, metal mesh, polymer mesh, braided wire, woven wire, braided polymer, woven polymer, nonwoven polymer, and combinations thereof.

5. The medical device of claim 1, wherein the plurality of device anchors are further coupled to the device frame.

6. The medical device of claim 1, wherein the plurality of device anchors comprises a plurality of hooks.

7. The medical device of claim 6, wherein the plurality of hooks has at least one of:
    varying sizes; and
    varying hook geometries.

8. The medical device of claim 1, wherein the plurality of device anchors comprises a plurality of barbs.

9. The medical device of claim 8, wherein the plurality of barbs has at least one of:
    varying sizes; and
    varying orientations.

10. The medical device of claim 1, wherein the plurality of device anchors comprises at least one hook and at least one barb.

11. The medical device of claim 1, wherein each of the plurality of device anchors is formed from at least one of nitinol, stainless steel, and a polymer.

12. The medical device of claim 1, wherein each of the plurality of device anchors is sewn onto the device frame and extends outwardly through the corresponding channel of the plurality of channels of the at least one fabric layer.

13. The medical device of claim 1, wherein each of the plurality of device anchors is injection molded directly onto the device frame and extends outwardly through the corresponding channel of the plurality of channels of the at least one fabric layer.

* * * * *